United States Patent
Coupland et al.

(10) Patent No.: US 6,912,891 B2
(45) Date of Patent: Jul. 5, 2005

(54) CHARACTERIZATION OF FLUIDS USING ULTRASOUND

(75) Inventors: John N. Coupland, State College, PA (US); Raffaella Saggin, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 165 days.

(21) Appl. No.: 10/177,694

(22) Filed: Jun. 21, 2002

(65) Prior Publication Data

US 2003/0051535 A1 Mar. 20, 2003

Related U.S. Application Data

(60) Provisional application No. 60/300,212, filed on Jun. 22, 2001.

(51) Int. Cl.[7] .......................... G01N 29/00; G01N 37/00
(52) U.S. Cl. ....................................... 73/64.53; 73/61.45
(58) Field of Search ............................. 73/64.53, 61.45, 73/61.75, 61.79, 24.01, 24.04, 24.03, 24.05, 24.06, 1.82

(56) References Cited

U.S. PATENT DOCUMENTS

| | | | |
|---|---|---|---|
| 3,553,636 A | | 1/1971 | Baird |
| 4,014,650 A | * | 3/1977 | Sigelmann ................ 73/64.42 |
| 4,182,155 A | * | 1/1980 | Fowler ........................ 73/1.81 |
| 4,384,476 A | * | 5/1983 | Black et al. ............... 73/61.79 |
| 4,509,360 A | * | 4/1985 | Erwin et al. ............... 73/61.75 |
| 5,365,778 A | | 11/1994 | Sheen et al. |
| 5,467,321 A | | 11/1995 | Baumoel |
| 5,616,872 A | * | 4/1997 | O'Brien ..................... 73/61.75 |
| 5,686,661 A | | 11/1997 | Singh et al. |
| 5,708,191 A | | 1/1998 | Greenwood et al. |
| 5,739,432 A | * | 4/1998 | Sinha .......................... 73/579 |
| 5,777,230 A | * | 7/1998 | Vandervalk .................. 73/632 |
| 5,853,994 A | * | 12/1998 | Gopinathan et al. ....... 73/61.75 |
| 5,969,237 A | * | 10/1999 | Jones et al. ................ 73/61.75 |
| 6,032,516 A | * | 3/2000 | Takahashi et al. ......... 73/64.53 |
| 6,082,181 A | | 7/2000 | Greenwood |
| 6,227,040 B1 | | 5/2001 | Hastings et al. |

OTHER PUBLICATIONS

McClements et al. "Ultrasonic Analysis of Edible Fats and Oils", Ultrasonics, 1992 (no month), vol. 30, No. 6, pp. 383–388.*
McClements et al., "Ultrasonic Pulse Echo Reflectometer," Ultrasonics vol. 29 pp. 58–62, 1991.
McClements et al. , "Frequency Scanning Ultrasonic Pulse Echo Reflectometer," Ultrasonics vol. 30, N06, pp. 403–405, 1992.
Povey, "Ultrasonic Determination of the Properties of Food Dispersions," Sem Food Anal 4(2):95–111, 1999.
Saggin et al., "Concentration Measurement by Acoustic Reflectance," Journal of Food Science vol. 66 No. 5, pp. 681–685, 2001.

* cited by examiner

Primary Examiner—Edward Lefkowitz
Assistant Examiner—Michael Cygan
(74) Attorney, Agent, or Firm—McQuaide, Blasko, Schwartz, Fleming & Faulkner, Inc.

(57) ABSTRACT

A method of using ultrasonic reflectance to characterize physical properties of fluids, particularly food solutions. In general, the method comprises the steps of: (a) generating longitudinal ultrasonic waves, (b) coupling the transducer to the fluid being investigated, (c) detecting the reflected longitudinal waves, and (d) determining the physical property of interest by correlating certain characteristics of the reflected ultrasonic waves with the physical property being measured. A particular aspect of the invention is a self-calibrating ultrasonic device useful as a solids concentration sensor and/or a dissolution/precipitation sensor. Self calibration is accomplished via a twin delay line. The invention is particularly useful as an on-line sensor in the processing of food solutions such as milk, ketchup, syrup, chocolate and other confectionary.

10 Claims, 8 Drawing Sheets

CHARACTERIZATION OF FLUIDS USING ULTRASOUND

BENEFIT OF PRIOR APPLICATION

This application claims the benefit of prior filed U.S. Provisional Patent Application No. 60/300,212 filed Jun. 22, 2001.

GOVERNMENT SPONSORSHIP

This work was supported by the United States Department of Agriculture under the Hatch Act project numbers PEN03591 and PEN03697. Accordingly, the US government may have certain rights in this invention.

FIELD OF THE INVENTION

The invention relates to the characterization of liquids (including liquids containing solids) using ultrasonic reflectance. More particularly the invention relates to the use longitudinal ultrasonic wave reflectance to determine certain fluid properties that are directly and indirectly related to bulk modulus and density of the fluid.

BACKGROUND OF THE INVENTION

There has long been a need in industries that handle fluid materials for devices and systems that can measure or estimate properties and conditions of the fluids being handled. Such information can provide a number of benefits including: safer handling of materials, better product quality, lower costs of production, and increased efficiency. There are many properties that can be measured or estimated using such characterization devices. Some commonly measured properties are temperature, pressure, fluid flow rate, density, viscosity, and acidity.

Physical property measurement devices and techniques are used in many industries including, for example, plastics manufacture, petroleum refining, pharmaceuticals manufacture, and food processing, which is a preferred application of the present invention. In food processing, it is very common to process fluid foods and to have a need to determine or estimate the physical properties of the fluid. Some foods processed in fluid form include milk, ketchup, juices, syrups, chocolate and other confectionary, etc. In the processing of such foods, any number of physical properties of the food can be of interest including those properties mentioned above. However, particular properties that are of special concern to the present inventors are solids content and state of dissolution of added solid ingredients or precipitation of solids from the melt. A primary reason for monitoring such properties is to ensure product quality and consistency.

Methods for determining fluid properties can be classified into two types: off-line and on-line procedures. With off-line techniques a sample is typically removed from the system and the desired information is extracted from the sample using a separate device, which is often at a separate location. Off-line methods are generally more labor intensive and take longer to get results. On-line methods are integrated into the processing system itself and generally do not disturb the flow of the process or require removal of a sample. Further, on-line methods typically can provide frequent or even continuous monitoring of the desired property in real time. Thus, on-line techniques are usually preferred over their off-line counterparts and on-line processing is a preferred application of the present invention.

Process control is fairly common in fluid processing and methods and devices to measure many fluid properties have been created. The most commonly used process control systems involve measurement of pressure and temperature but others are known. For example, various on-line techniques have been used to measure solution concentration. Perhaps the most widely used (to measure solution concentration) is the refractive index determination, but a disadvantage of this method is that it requires glass or other transparent material to be brought into contact with the food item. This can raise the complexity and cost of designing and manufacturing the system. Another technique uses conductivity (or other electrical property) measurements to determine the concentration of some solutions.

Other technologies known to be used to characterize food include infrared spectroscopy and nuclear magnetic resonance. These are often used for rapid and nondestructive characterization of foods. Both methods can determine the composition of foods but both are fairly expensive and are not always readily applicable online.

Another technology that has been variously applied to measure fluid properties is ultrasound. Ultrasound consists of high frequency (>20 kHz) sound waves that propagate in materials as small deformations in their structure. Because of this, the capacity of a material to support an acoustic wave as measured as the velocity, attenuation or impedance, is sensitive to both composition and microstructure. There are generally two types of ultrasound waves that can be produced: shear waves and longitudinal waves. In shear waves the deformations are normal to the direction of propagation while in longitudinal waves the deformations are parallel to the direction of propagation. The present invention is primarily concerned with longitudinal waves.

The two general types of ultrasound measurement techniques available are transmittance and ultrasonic reflectance. Ultrasonic transmittance gains useful information about a fluid or other material by measuring how ultrasonic waves are effected as they travel through the material. In ultrasonic reflectance methods, useful information is gained by measuring how ultrasonic waves are effected when the are reflected off of a material to be investigated. Information is gained from the change in signal amplitude and phase following reflection and both parameters may depend usefully on the frequency of the sound. Such changes can then be used to calculate values for various physical properties of the material that are known to correlate linearly or non-linearly with such changes. A potential disadvantage of ultrasonic transmittance methods is that measurement requires the propagation of the sound across a known and fixed distance. This is easy to achieve in a laboratory instrument but it is often a problem in an on-line application where existing equipment may have to be replaced or extensively modified to allow the fitting of the transducers. Reflectance measurements enjoy the key advantage of requiring no modifications of existing equipment.

Ultrasound technologies have many desirable characteristics that make them useful as an on-line sensor (Povey M. "Ultrasonic determination of the properties of food dispersions" Sem Food Anal 4 (2):95–111, 1999). The equipment is relatively inexpensive and robust, the measurements are simple and easily automated, and the sonic beam can pass through container walls and opaque fluids. However, despite this recognition of the benefits of using ultrasound techniques for measuring certain properties of foods, on-line ultrasonic measurements are not widely used for measuring physical properties of food solutions. A possible reason is the disadvantages of transmittance techniques which require that the ultrasound waves must travel a precise and known distance through the sample.

Some particular patents directed at using ultrasound to measure fluid properties in industrial processes in general include U.S. Pat. No. 5,365,778 to Sheen et al. ("Sheen"), U.S. Pat. No. 5,467,321 to Baumoel, U.S. Pat. No. 5,686,661 to Singh et al. ("Singh"), U.S. Pat. No. 6,082,181 to Greenwood ("Greenwood '181"), U.S. Pat. No. 5,708,191 to Greenwood ("Greeenwood '191") and U.S. Pat. No. 6,227,040 to Hasting et al. ("Hastings"). These patents are hereby incorporated by reference.

The Sheen patent discloses an ultrasonic viscometer and method for measuring fluid viscosity. In this method, ultrasonic shear and longitudinal waves are generated and coupled to the fluid. Ultrasonic shear and longitudinal wave reflections are then detected. From the reflected longitudinal waves, phase velocity of the fluid is determined and from the shear waves viscosity of the fluid is determined. This patent also discloses a self-calibration technique. The primary application of the Sheen technology is for determining viscosity of coal slurry processes.

The Baumoel patent teaches an insertion type ultrasonic transducer assembly adapted to be mounted to a pipe for determining ultrasonic energy transit time through fluid in the pipe. This patent differs from the present invention in that it is concerned only with transmittance of ultrasound shear waves through the fluid whereas the present invention is limited to reflectance of preferably longitudinal waves. Further, the Baumoel patent discusses a common use of ultrasound for determining fluid flow rates and does not address the use of ultrasound in fluid food processing.

The Singh patent discloses a laser enhanced ultrasound method and device for remotely measuring the viscosity of molten materials such as melt glass, melt alloys and the like during processing of the materials. Again this process uses shear waves and is concerned with transmittance of ultrasound through the fluid unlike the present invention. In addition, this patent does not discuss food solutions or making the type of physical property measurements addressed by the present invention.

The Greenwood patents disclose ultrasonic fluid densitometers. The invention includes a wedge having at least two transducers for transmitting and receiving ultrasonic signals internally reflected within the material wedge. It is taught that the wedge should have an acoustic impedance close to that of the fluid being tested.

The Hasting patent discloses an apparatus for determining the viscosity of a fluid in a container such as a tank or pipe. This patent is concerned with ultrasonic transmittance through the fluid.

Despite the broad interest in developing ultrasonic measurement techniques for fluid properties, as indicated by the variety of patents and examples given above, there continues to exist a need for improved techniques and devices. There especially exists a need for improved devices in the food processing industry and particularly for on-line methods. These are the primary needs addressed by the present invention.

Accordingly, it is an object of the present invention to provide an ultrasound method and device to measure certain physical properties of fluids.

It is an additional object of the present invention to provide an ultrasound device that is self calibrating.

Further, it is an object of the present invention to provide an on-line sensor for measuring physical properties of food solutions.

SUMMARY OF THE INVENTION

A method of using ultrasonic reflectance to characterize physical properties of fluids, particularly food solutions. In general, the method comprises the steps of: (a) generating longitudinal ultrasonic waves, (b) coupling the transducer to the fluid being investigated, (c) detecting the reflected longitudinal waves, and (d) determining the physical property of interest by correlating certain characteristics of the reflected ultrasonic waves with the physical property being measured. A particular aspect of the invention is a self-calibrating ultrasonic device useful as a solids concentration sensor and/or a dissolution/precipitation sensor.

DETAILED DESCRIPTION OF THE INVENTION

Figure 1A:
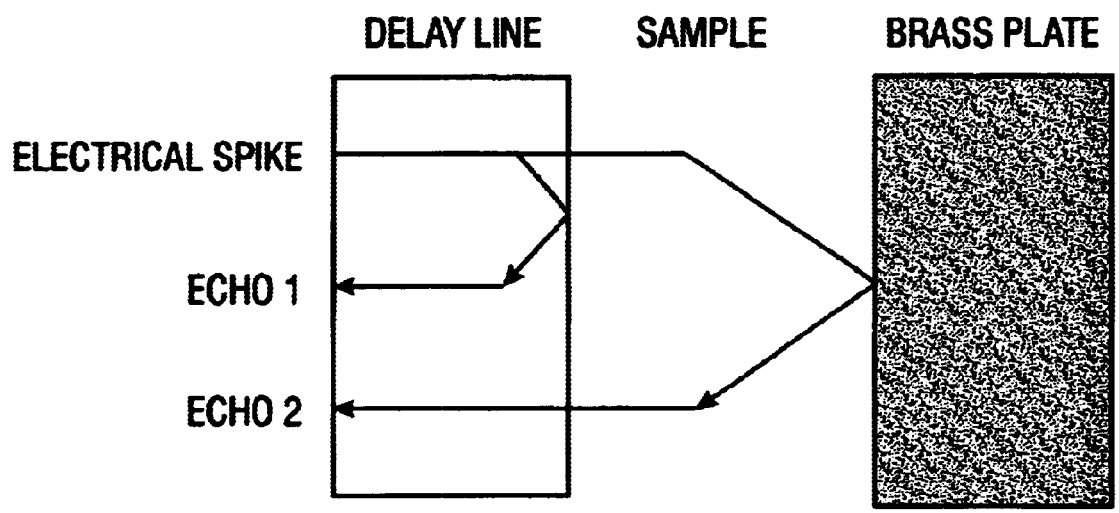
FIG. 1a is a diagram showing the acoustic path of the signals measured.

The present inventive method and the apparatus underlying the method can generally be described as consisting of four parts. These are the following:

a) generating ultrasonic longitudinal waves;
b) coupling the generated waves with the fluid to be investigated so that the waves can be reflected from the fluid interface;
c) detecting the reflected waves; and
d) processing the information gained from detecting the reflected waves in a manner that leads to a value being produced for the desired physical property being investigated.

An optional, but preferred, additional step involves either normalizing the detected waves with a standard measurement or using a self calibration step. Each of these parts of the invention will now be discussed in more detail.

The first step in the process is to generate ultrasonic longitudinal waves. The specific characteristics of the waves generated is not critical as long as the waves are capable of traveling to the fluid interface and capable of being reflected and meaningfully detected (e.g. the signal is received with sufficient strength and clarity). Thus the specific frequency, pulse rate, etc. can be varied widely to optimize the results. The wave is generally produced in a pulse primarily to allow time-resolution of the generated and detected signal and sometimes to simultaneously generate a range of frequencies. Also, with a pulse, the deformations associated with the wave are small and thus non destructive to the apparatus or sample. Unlike some prior art techniques, the present invention preferably uses only longitudinal waves and not shear waves. The transducer used to generate the ultrasound can be any commercially available transducer capable of generating such waves and is thus not particularly limited.

The second step of the process is coupling the longitudinal wave generating transducer to a solid object in contact with the fluid to be investigated. This solid object is essentially a "delay line" through which the ultrasonic waves travel before reaching the fluid interface where they are partially reflected back through the delay line before being detected. The delay line is a material through which the ultrasound wave will pass through and cause a time delay in the reflected echoes. There are many options for the design of the delay line. A key advantage of the method of the invention is that the delay line used in one embodiment can be the wall of any food processing equipment or packaging (e.g. tank or pipe wall). The transducer is simply attached to the outer wall of the equipment, either by physical coupling or merely pressing the sensor in place by hand. The ultrasonic pulse travels through the wall, reflects from the food surface and the returning signal can be instantaneously converted to a solids content measurement.

In another embodiment of the invention, the delay line is directly connected to the exposed end of the transducer to essentially create a probe. This probe can then be inserted into the fluid to be investigated at will or can be installed fixedly into the fluid processing system so that it is in continuous contact with the fluid. In this embodiment the delay line is a small object usually similar in size and shape to the transducer being used (e.g. disc like). Note that when the transducer is fixedly coupled to a fluid processing system, the device is essentially an on-line sensor and this coupling of the transmitted longitudinal waves with the delay line becomes inherent in the operation of the sensor.

Figure 10A:
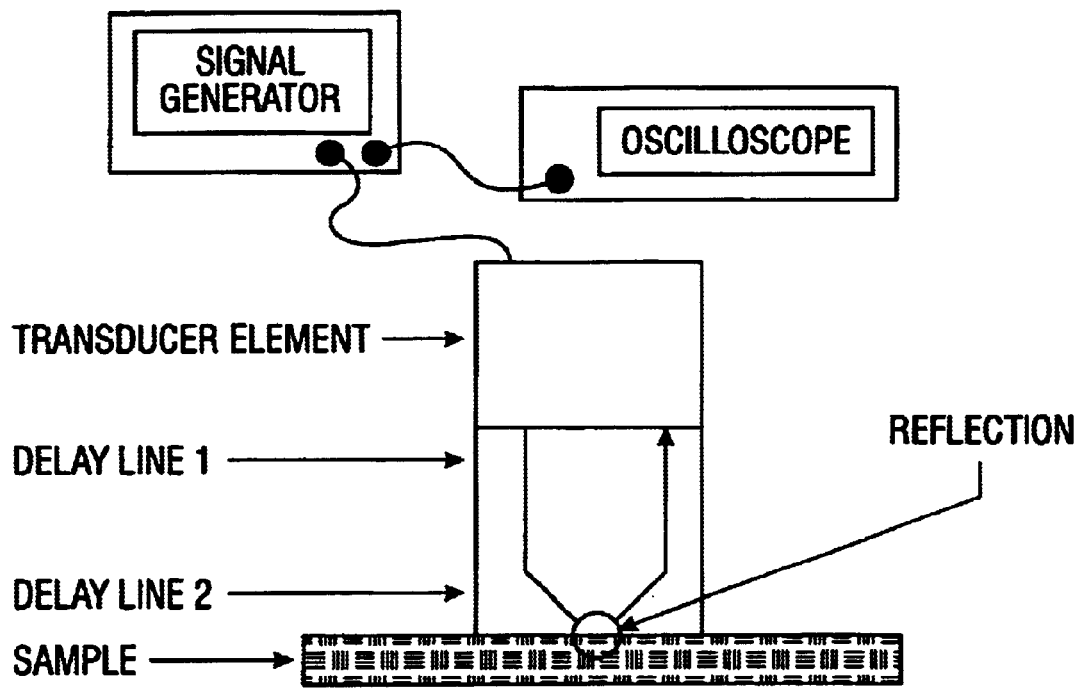
FIG. 10 is a schematic illustration of the delay line configurations described below: (a) Single delay line so only one echo is measured. The magnitude of the echo depends on the magnitude of the pulse generated and on the acoustic properties of the sample so requires a calibration to measure the latter. (b) A twin delay line produces two echoes so the two unknowns can be solved simultaneously obviating the need for an external calibration.
Figure 10B:
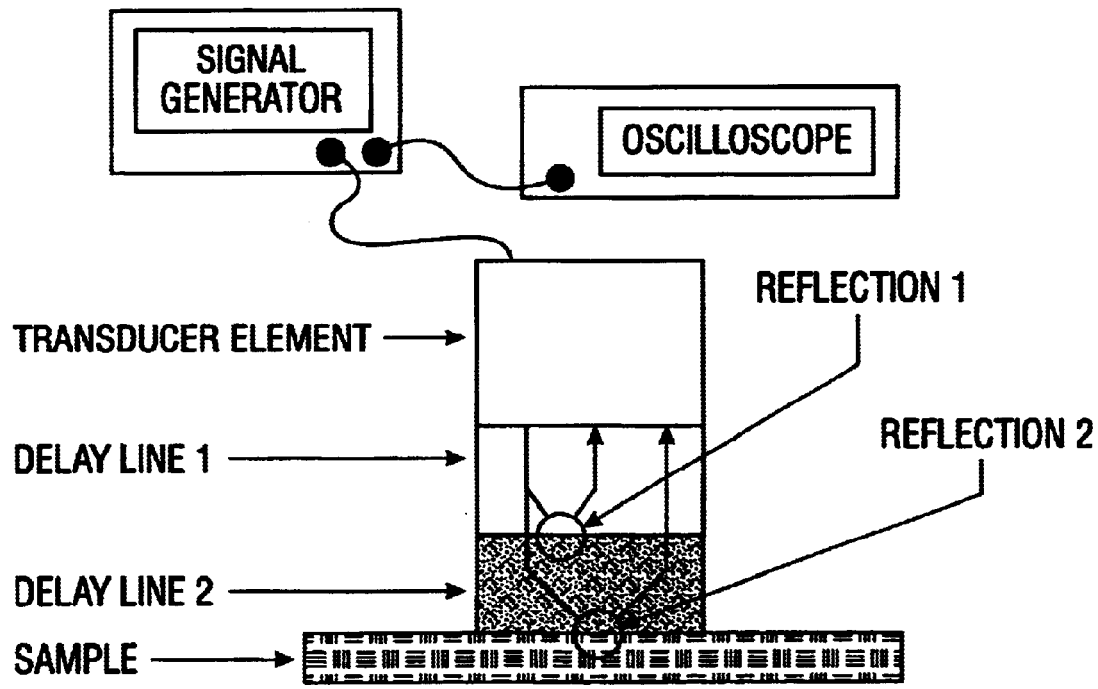

In a preferred embodiment of the invention, the delay line actually consists of two separate materials so that a reflectance is produced at the interface of the two materials as well as at the interface of the fluid surface. This embodiment is represented by FIG. 10(b) and is an additional novel aspect of the invention. The use of two different delay lines produces two different reflections which can be used to self calibrate the device as will be more fully explained below in Example 3. Note that the interface of the two materials in the twin delay line only partially reflects the ultrasonic wave allowing waves to continue through the second material and to be reflected (again in part) at the fluid interface.

The material used for the delay line can theoretically be any material that is capable of efficiently transmitting longitudinal ultrasound waves. The best materials are generally metals such as stainless steel, aluminum, brass, and the like as well as polymers (e.g., Plexiglas™, and polystyrene). In the twin delay line embodiment the two delay lines are made from two different selections of these materials. It is desirable to have the second delay line (the one in contact with the fluid sample) to be made of a material that has an ultrasonic impedance value that is close to that of the fluid sample. By "close to" is meant within a ratio of 1:5 to 5:1 preferably within about 1:2 to 2:1. It is even more preferred that they are as close as possible without being identical. For typical aqueous food solutions discussed herein the optimal acoustic impedance for the twin delay line with longitudinal waves is around 5.5 MRayl. Possible good choices are Araldite™ (Vantico, Inc.), graphite and Dow epoxy resin.

Another design parameter for the delay line is the thickness of the delay line. The thickness in the delay line does make a difference as the thicker the material the longer it will take for the ultrasound waves to travel through the delay line. Optimal or preferred thickness values will depend to some extent on the ultrasonic velocity and attenuation of the delay line material. However, in general we can say that a preferred thicknesses will be sufficient to allow resolution of the reflectance peaks of interest and hence depend on the speed of sound in each material.

The third step in the process is to detect the reflected ultrasonic waves. The detecting transducer is typically the same one that generates the sound waves. The detector will measure the time-amplitude signal returning to the transducer and separate out the wave envelopes of interest (i.e., those corresponding to the relevant echoes). This information is then passed on to electronic circuitry or other devices that can process this information into measurement values for the desired parameters which is the next step of the process.

Figure 2:
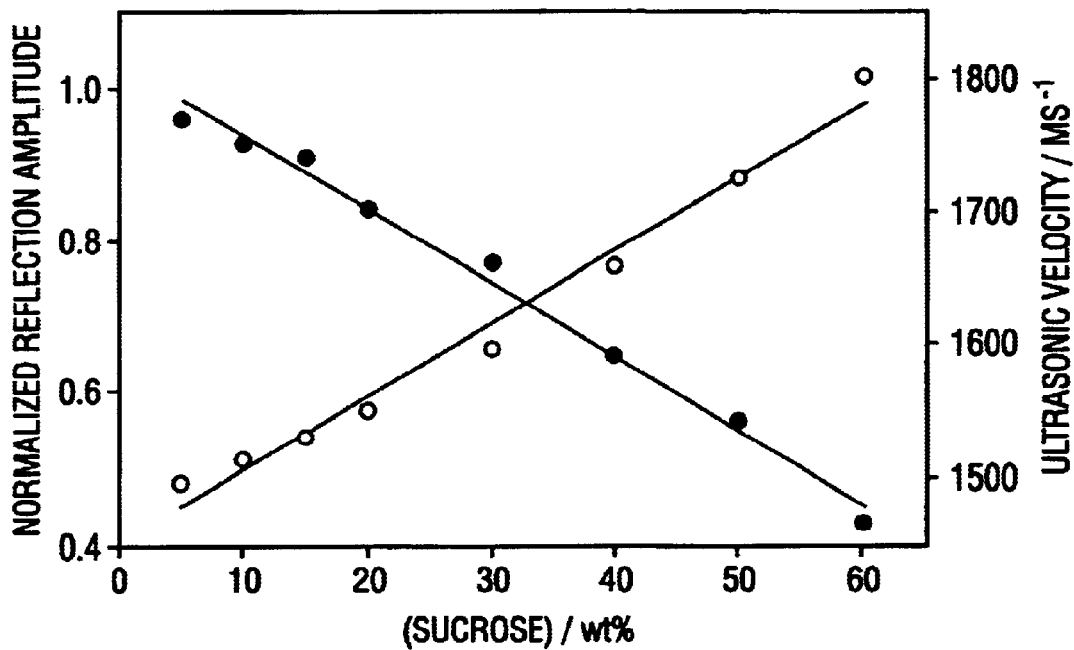
FIG. 2 shows normalized reflection amplitude (●) and ultrasonic velocity (○) as a function of sucrose concentration.
Figure 3:
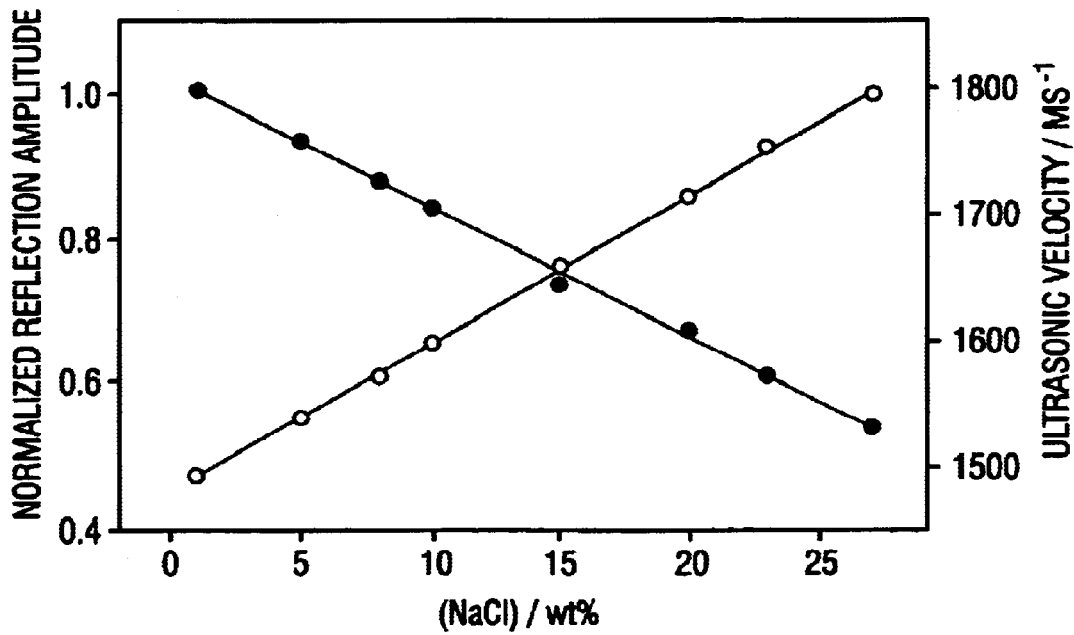
FIG. 3 shows normalized reflection amplitude ( ) and ultrasonic velocity (○) as a function of sodium chloride concentration.
Figure 4:
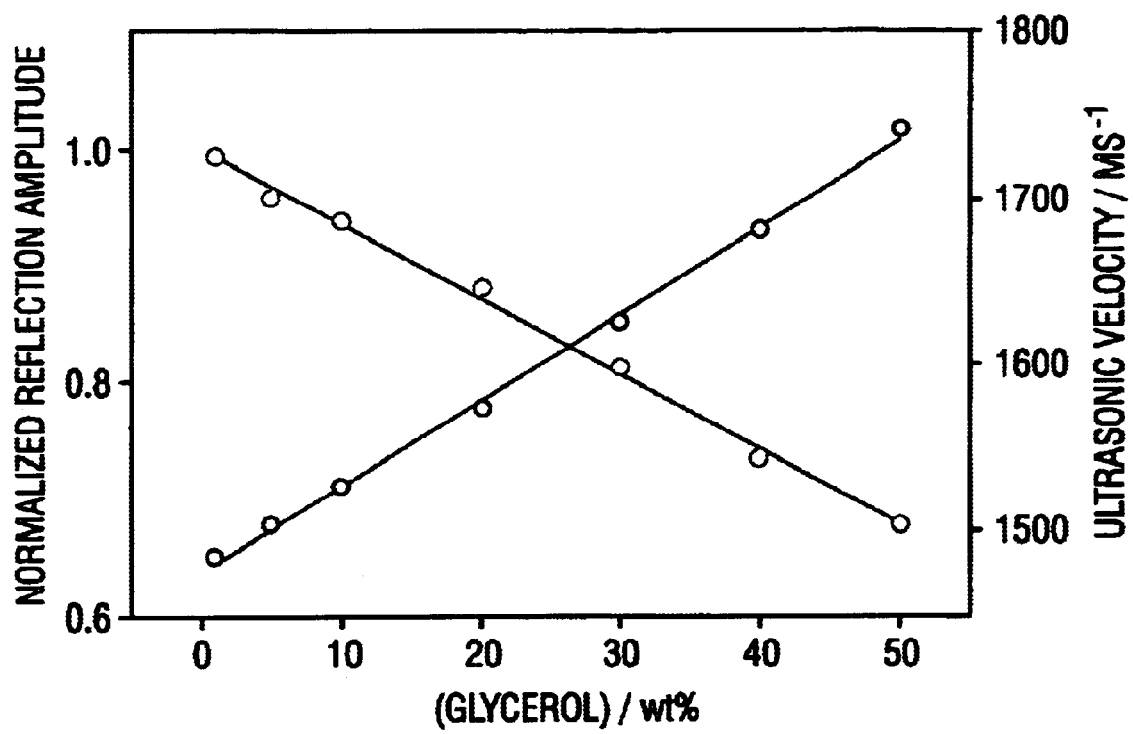
FIG. 4 shows normalized reflection amplitude (●) and ultrasonic velocity (○) as a function of glycerol concentration.
Figure 5:
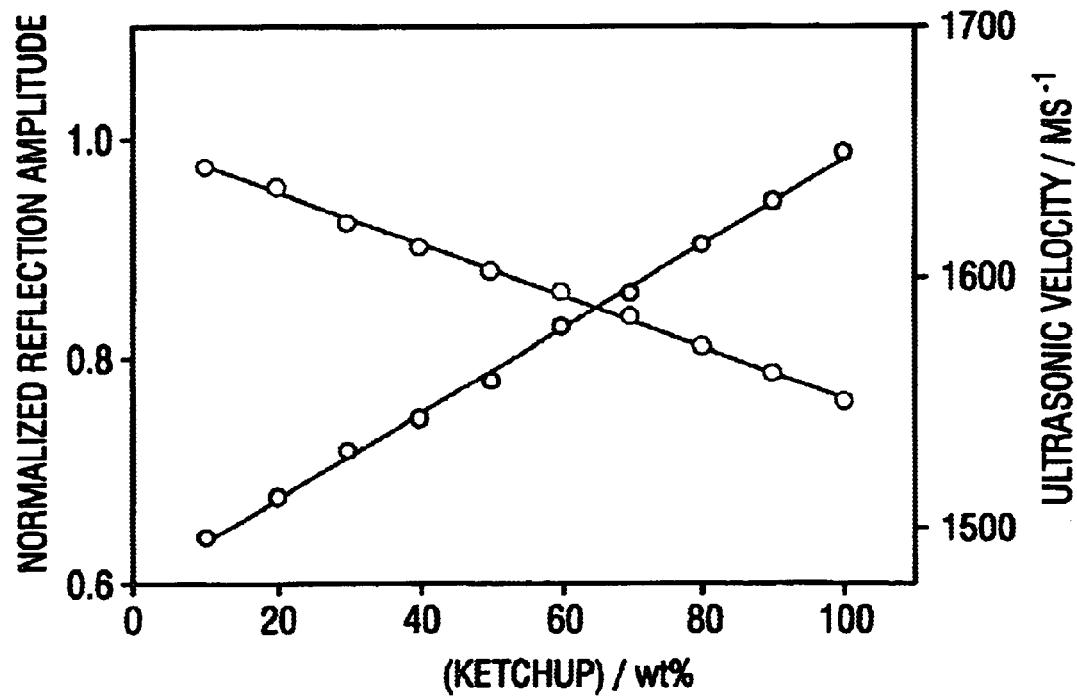
FIG. 5 shows normalized reflection amplitude (●) and ultrasonic velocity (○) as a function of tomato ketchup concentration.

The final step in the method of the invention is processing the information gained from detecting the reflected waves in a manner that leads to a value being produced for the physical property being investigated. In general the peak-to-peak voltage is extracted from the received data and is compared with empirically predetermined values which will correlate a specific voltage value with a specific value for the physical property being measured. The voltage value can provide a reading from a chart like that in FIG. 2 or it can be used to calculate a value from a previously determined linear or non-linear equation that models the behavior of the physical property (see Example 1).

An optional, but preferred, step in the process is to either normalize the detected echoes with a standard or perform a self calibration process. The voltage amplitude values will typically be normalize to the voltage values obtained from echoes reflected from a standard fluid (e.g. water). This will obviate any fluctuations in the power of the transmitted ultrasonic waves. An even more preferred embodiment of the invention uses a self-calibrating technique to avoid the necessity of a separate standard run. This self-calibration process uses a twin delay line mentioned above wherein the transmitter is connected to the first delay line material which is connected to the second delay line consisting of a different material which is in contact with the fluid sample when in operation. This produces an additional reflected echo from the interface of the two delay lines. This additional echo can be used to, in effect, normalize the echo from the fluid interface as discussed in more detail in Example 3 below.

EXAMPLES

As the examples below will demonstrate, ultrasonic reflectance is a precise and reliable method for measuring food solution characteristics. Characteristics of fluid foods containing solids can be achieved to comparable precision using ultrasonic reflectance as it can be by ultrasonic transmittance which has significant disadvantages. For example, measurements in combination with appropriate calibration can estimate the solids content of a food solution to within approximately ±3% standard error of the true value.

The present invention is concerned solely with the use of ultrasonic reflectance from (and not transmittance through) the sample being investigated. This sensing modality enjoys all of the advantages of conventional ultrasonic transmission (i.e., velocity and attenuation) measurements and additionally there is no requirement for a receiving transducer or a parallel reflecting plate a known and constant distance apart. An additional advantage is that there is little or no need for modification of existing equipment in order to use the invention in a working plant under real conditions without interrupting normal production. These and other advantages are demonstrated by the following examples.

Example 1

Solid Concentration Measurement

It has long been appreciated that the speed of sound in a fluid changes with concentration (solids content) of a given material and, having generated a suitable calibration curve, it is possible to relate ultrasonic measurements to concentration with good precision (Basaran T K et al., "Monitoring molecular diffusion of sucrose in xanthan solutions using velocity measurements" J Food Sci 64 (1):125–128, 1999). However, it has not previously been appreciated that an ultrasonic reflectance technique based on impedance could be used in this capacity.

This example demonstrates that ultrasonic reflectance can provide equally precise measurements of concentration as conventional ultrasonic velocity (transmittance) measurements. The speed of sound (prior art method) and the acoustic reflection coefficient (present invention) of sucrose (0–60 wt %), glycerol (0–50 wt %), sodium chloride (0–27 wt %) solutions and tomato ketchup (0–100 wt %) dispersions were measured using a modified pulse echo technique (2.25 MHz transducer, 20° C.). All measured parameters are linear functions of concentration. For all samples except for concentrated ketchup (>50 wt %) measured reflectance is demonstrated to be a function of ultrasonic velocity and density.

Tomato ketchup (Heinz™ brand, 24 oz. polyurethane bottle) was purchased from a local supermarket. All other reagents were purchased from the Sigma Chemical Company (St. Louis, Mo.). Solutions were prepared with distilled water. Solutions were prepared on a weight basis as grams of solid per total mass. The ketchup was assumed to be a pure solid, i.e., a 10% ketchup solution was 10 g of ketchup in 90 g of water. All measurements were conducted at 20.0+/−0.1° C.

The density of samples was measured using a vibrating tube densitometer (Mettler Toledo DE51 Density Meter). This device consisted of a thermostatically controlled glass U-tube filled with the sample under investigation. An oscillating force was applied to the tube and the frequency of resonance measured. The resonance properties of the filled tube depend on its mass and, since the tube volume was known, the density of the fluid could be measured to very high precision. The instrument used in this case was accurate to +/−10 $\mu$g cm$^{-3}$. The measurements were extremely precise, typically +/−50 $\mu$g cm$^{-3}$.

Figure 1B:
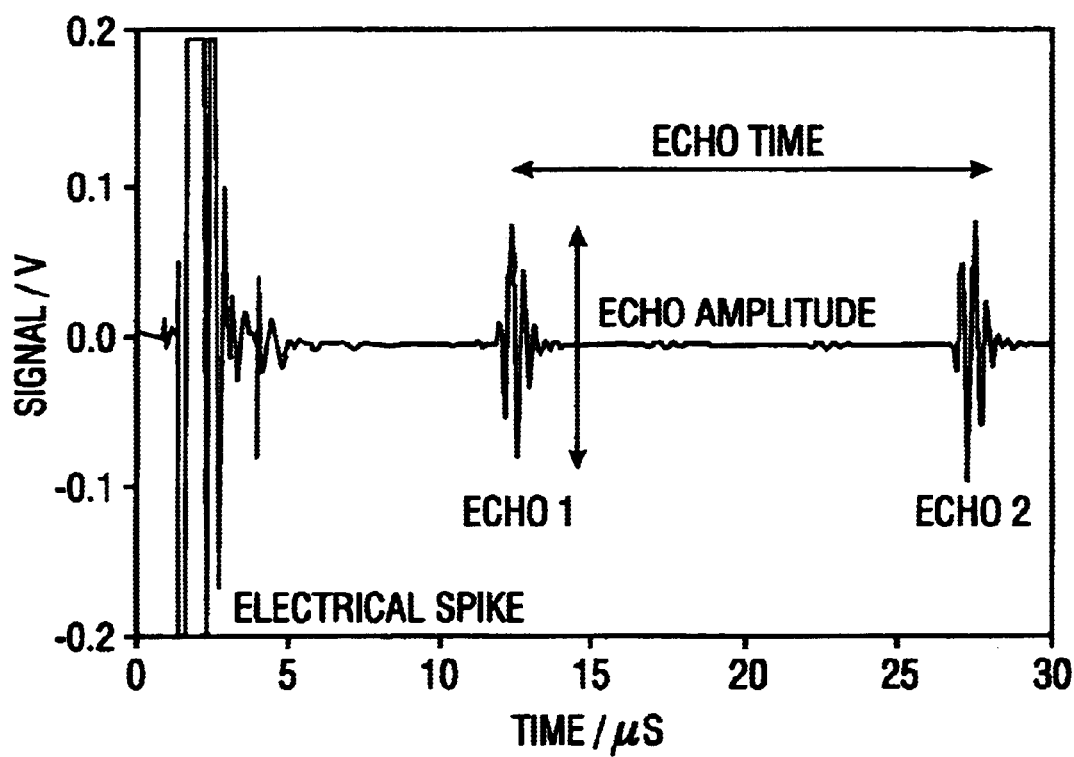
FIG. 1b shows a typical oscilloscope trace showing the peaks of interest.

The speed of sound (prior art) and reflection coefficient (present invention) was measured using a modified pulse-echo technique (McClements D J, et al., "Ultrasonic pulse echo reflectometer", Ultrasonics 29 (1): 58–62, 1991). The acoustic path and source of the reflections are illustrated diagrammatically in FIG. 1a. Note that Echo 1 is a reflected signal which is used in the present invention and Echo 2 is a transmitted signal which is used in prior art techniques and is shown for comparison. An electrical spike signal (Panametrics 500 PR, Waltham, Mass., U.S.A.) was passed to a 2.25 MHz broadband ultrasonic transducer (Panametrics V606) which converted the energy to ultrasound. The pulse of sound traveled into the Plexiglas delay line, and was partially reflected at the plastic-sample interface. The reflected part returned to the transducer and was re-converted to an electrical signal (echo 1). The transmitted part traveled through the sample, was reflected from the brass plate and returned through the sample and the delay line to the transducer (echo 2). A digital storage oscilloscope (LeCroy 9310c, Chestnut Ridge, N.Y., U.S.A.) was used to capture the data; the signals were averaged over 200 pulses to reduce signal noise. A typical oscilloscope trace is shown as FIG. 1b. The complete measurement took approximately 5 seconds to complete.

The time delay between echo 1 and echo 2 ($\Delta t_s$) is the time for the sound to travel through the sample twice. The speed of sound in the sample $c_s$ can be calculated from the measured time of flight in water ($\Delta t_w$) and the published (Del Grosso V A et al., "Speed of sound in pure water", J Acoust Soc Am 52 (5):1442–1446, 1972) speed of sound in water ($c_w$) using Equation 1:

$$c_s = c_w \frac{\Delta t_w}{\Delta t_s} \qquad [1]$$

The peak-to-peak amplitude of echo 1 depends on the magnitude of the generated pulse (a property of the apparatus) and the acoustic dissimilarity between sample and delay line (a property of the material under investigation). Because the magnitude of the generated pulse could not be relied upon as a constant on a day-to-day basis, the measured value was normalized to a similar measurement made against the calibration material (water). Alternatively it would have been possible to use the twin delay line configuration and eliminate the need for an external calibrant. All measurements were repeated at least four times.

The normalized reflection intensity (present invention) and ultrasonic velocity (prior art) are plotted against solids content for sucrose, sodium chloride, glycerol and ketchup solutions in FIGS. 2–5. In all cases the ultrasonic velocity increases and the reflection coefficient decreases with concentration. This first observation is consistent with the general rule that sound travels more rapidly through a solid than a liquid and measured velocity data are comparable with literature values. The data were empirically modeled using the simple linear function, $X = X_{water} + k\phi$, where X is the ultrasonic velocity (normalized reflection amplitude) of the sample, $X_{water}$ is the ultrasonic velocity (normalized reflection amplitude) of pure water, and $\phi$ is the solids content of the sample. The best-fit parameters of the equations are shown in Table 1. While this example used a linear function, other calibration appropriate functions can be used which can easily be determined by a person of ordinary skill in the art. Additionally, while water has been used as the calibration solvent in the examples, the inventive method is not limited to water as other solvents may be used.

TABLE 1

| | Ultrasonic Velocity | | Normalized Reflection Amplitude | |
|---|---|---|---|---|
| | k/ms$^{-1}$ | r$^2$ | k | r$^2$ |
| Sucrose | 5.35 ± 0.74 | 0.981 | −0.0094 ± 0.0007 | 0.994 |
| Sodium chloride | 11.67 ± 0.27 | 0.999 | −0.0172 ± 0.0002 | 0.999 |
| Glycerol | 5.09 ± 0.31 | 0.997 | −0.0068 ± 0.0002 | 0.999 |
| Tomato Ketchup | 1.67 ± 0.06 | 0.997 | −0.0029 ± 0.0001 | 0.999 |

Typical coefficients of variance for velocity measurement were 0.07% and for amplitude measurements 0.25%.

Figure 6:
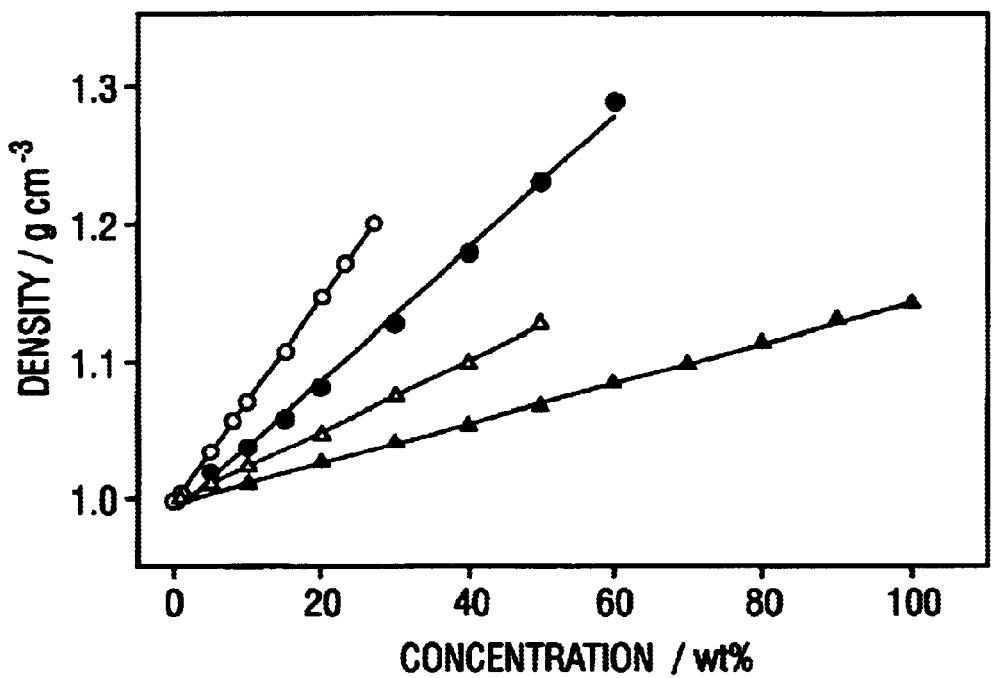
FIG. 6 is a plot of density as a function of concentration for sucrose (●), sodium chloride (○), tomato ketchup, (▲), and glycerol (Δ) solutions.

The densities of the solutions are plotted against concentration in FIG. 6. For each sample, the density of solutions was linearly related to concentration ($r^2$=0.999). The measured density of sucrose, sodium chloride and glycerol was in all cases very close to the literature values. No data on ketchup density was found in the literature.

We can use the data for the linear model presented in the Table 1 along with a measurement on an unknown sample to calculate its concentration. Consider, for example, a ketchup sample containing 40% added water. Using measured ultrasonic parameters, the tabulated correlation would estimate the solids content as 60.3±2.2% and 58.8±1.6% from velocity and reflectance measurements respectively. The variability of the two techniques was compared using the separate-variance t-test for independent samples and showed to be not significantly different (p>0.05). Therefore acoustic reflectance is an equally precise concentration measurement as ultrasonic velocity (similar conclusions can be drawn from other examples).

While this result has clear empirical value, there may be some concern as to which of the physical properties of the fluid are reflectance sensitive. When a wave traveling through medium 1 is normally incident upon a plane interface with medium 2, some of the sound energy is reflected and some transmitted. The proportion of energy reflected is the reflection coefficient R and is related to the impedance (z) of the sample as:

$$R_a = \frac{A_r^2}{A_i^2} = \left(\frac{Z_2 - Z_1}{Z_1 + Z_2}\right)^2 \quad [2]$$

$A_r$ and $A_i$ are the amplitudes of the reflected and incident sound waves respectively and the subscripts s and d refer to the sample and delay line. Adopting the superscript w for the water blank and s for the sample and rearranging Equation 2 (assuming $A_i$ is constant)

$$\frac{A_r^s}{A_r^w} = \frac{|z_d - z_s|}{|z_d + z_s|} \times \frac{|z_d + z_w|}{|z_d - z_w|} \quad [3]$$

The acoustic impedance is given by:

$$z = \frac{\omega \rho}{\kappa} \quad [4]$$

where $\omega$ is the angular frequency, $\kappa$ is the wave number, and $\rho$ the density of the medium. All material parameters are complex: composed of a resistive and reactive component however often the complex part of the equation can be neglected and then Equation 4 simplifies to z=$\rho$c (where c is the speed of sound). The normalized reflectance $$\left(\frac{A_r^s}{A_r^w}\right)$$

was calculated for all samples using Equation 3 from the measured speed of sound (FIGS. 2–5) and density (FIG. 6).

Figure 7:
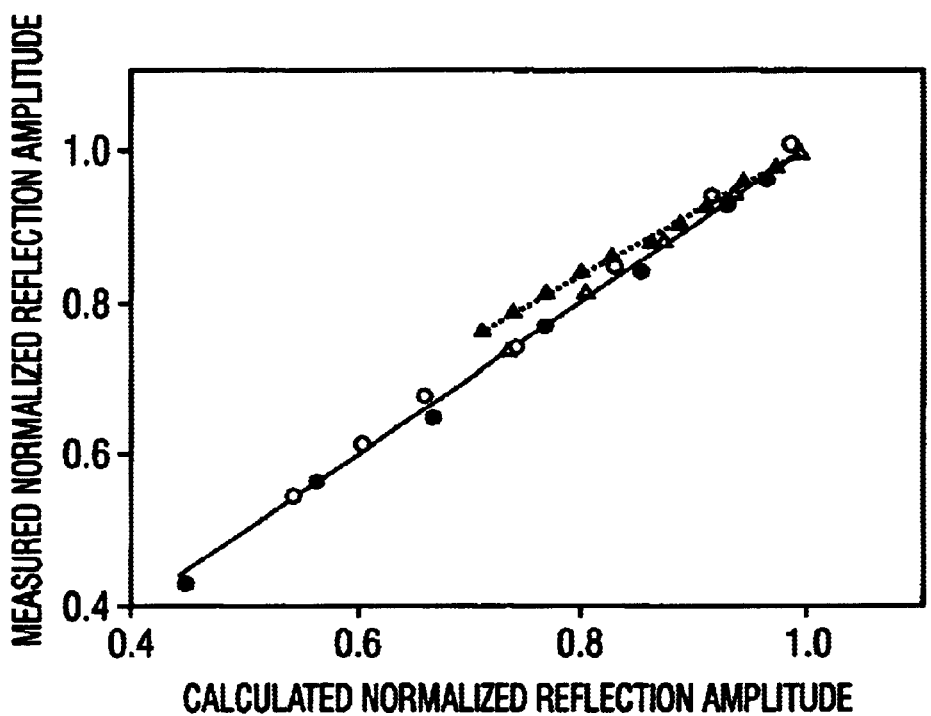
FIG. 7 is a plot of theoretically calculated against measured normalized reflection coefficient for sucrose (●), sodium chloride (○), tomato ketchup (▲), and glycerol (Δ) solutions. Solid and broken lines are general and ketchup-specific linear regressions as described in the detailed description.

The theoretically calculated reflection coefficient is plotted against the experimentally measured value for all samples (FIG. 7). The correlation between measured and calculated values was tested using regression models with indicator variables that contain interaction terms using commercial statistical analysis software (Minitab 12, Minitab Inc., State College, Pa., U.S.A.). This test was selected to determine whether all samples could be described using the same model. Once that the error term variances in the regression model for the two different populations were tested equal, the indicator variables were used to test the equality of the different regression functions. The measured and calculated values for sucrose, sodium chloride and glycerol solutions were similar (p>0.05) whilst there was no correlation for the ketchup solutions in the range of concentration considered (0–100%). However, when the test was repeated using only the diluted ketchup samples (0–50%), these data correlated with the general model. The solid line in FIG. 7 is a general regression for all samples except concentrated (>50 wt %) ketchup and shows that for many samples, reflectance is sensitive purely to the resistive impedance (=$\rho$c) of the samples. The broken line is a linear regression for all the ketchup samples.

As we have shown here, resistive impedance changes with composition so acoustic reflectance is a reliable concentration sensor, which is based on similar principles to ultrasonic velocity measurement. However, the resistive model becomes unreliable when the concentration of ketchup samples increases above 50%. This is probably because tomato particles in the sample scatter sound significantly and become a reactive component to impedance. In these cases reflectance will be also sensitive to structural parameters of the samples (e.g. particle size) as well as composition. Even when the resistive model is no longer applicable the linear regression in FIG. 5 retains its practical value for concentration measurement.

Example 2

Dissolution Measurement

In another area of concern in the food industry (and in the pharmaceutical industry as well), powder ingredients must often be completely redissolved in water or other solvents prior to further processing. In other cases, controlled formation of a powder from a saturated solution is needed to concentrate an industrial product, for example during the manufacture of sucrose or lactose or in the fractionation of fats. Thus measure of the amount of proportion of solids in liquid is a common need.

In current techniques for obtaining such information, it is common practice to separate the dissolved and undissolved portions by filtration or sedimentation prior to off-line analysis. These are off-line measurements which are in their nature intrusive and slow. Light scattering or NMR can also be used to study powder dissolution. Light scattering is only applicable for clear (i.e. dilute) samples and cannot be made easily inside typical process equipment. NMR instrumentation is expensive; the measurements are often relatively slow and cannot be made on material inside metallic containers.

An on-line sensor to track the dissolution/precipitation kinetics would allow automation of such operations and reduce waiting times. As demonstrated by this example, ultrasonic resonance is not sensitive to the presence of undissolved powder and can thus be used as a dissolution/precipitation sensor. Here we show that the concentration sensor is a function solely of dissolved material so we can determine the proportion of crystals dissolved without requiring a separation step.

Figure 8:
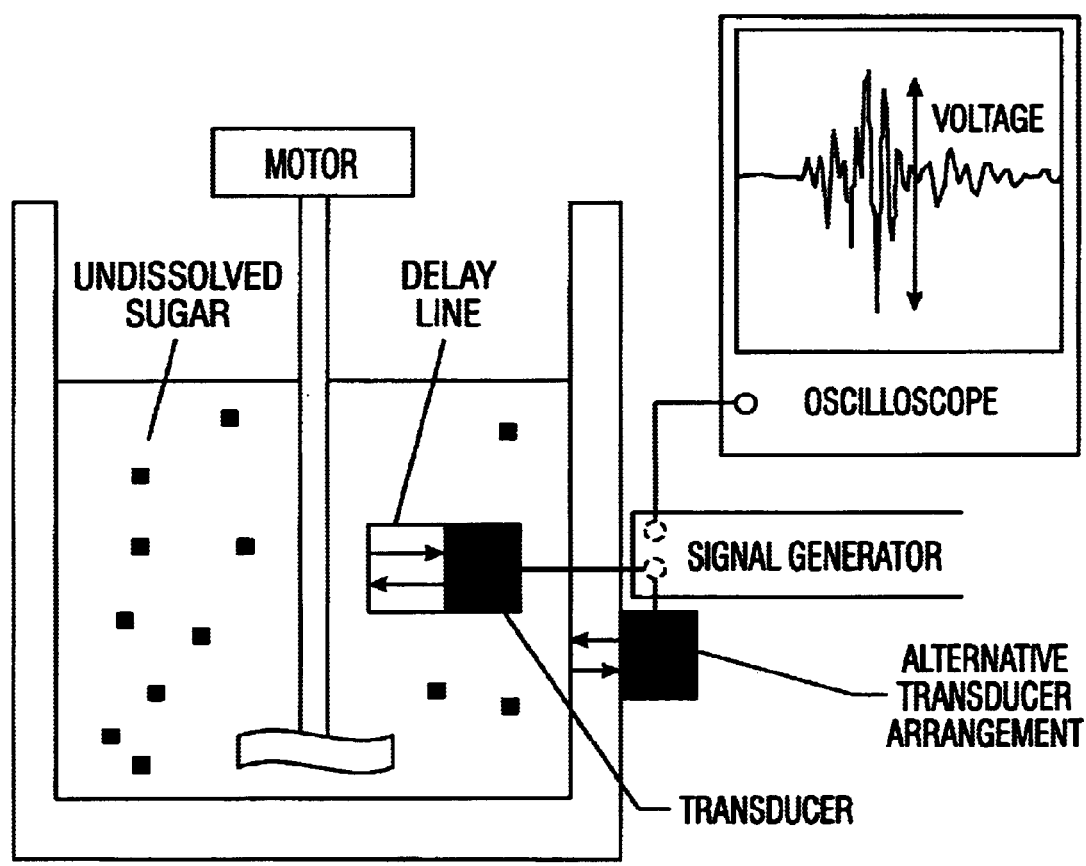
FIG. 8 is a schematic representation of an embodiment of the present invention. The reflectance coefficient, obtained from the amplitude (voltage) of the signal and normalized to a similar reading for water, is sensitive to the dissolved but not the undissolved materials.

A thermostatted (2, 20 and 60° C.) vessel was stirred at high speed with a rotating paddle. An ultrasonic transducer (2.25 MHz) was coupled to a polymer delay line, the other end of which was brought in contact with the stirred liquid. A pulse of sound was transmitted along the delay line and the magnitude of the echo returning from the liquid interface was measured (FIG. 8). The reflection coefficient was defined as the peak-to-peak amplitude of the received echo normalized to a similar reading from water.

Water (480 g) and sucrose or lactose (120 g) particles of known size distribution were mixed in the vessel and the ultrasonic reflection coefficient measured over time. Samples of particles and solution were taken at intervals during this process using a syringe, rapidly filtered and the dissolved sugar concentration measured using refractive index measurements.

Figure 9A:
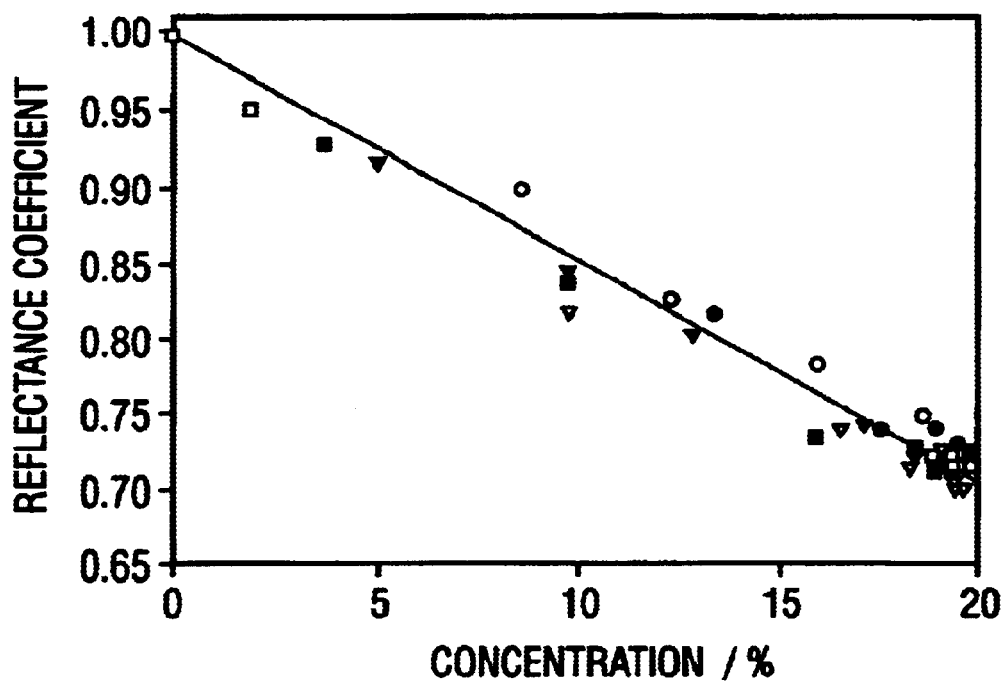
FIG. 9 shows reflectance plotted as a function of instantaneous dissolved (a) sucrose or (b) lactose concentration (20% wt sucrose or 10% wt lactose was added to the solution at the start of the experiment). Measurements were taken at various times during the dissolution process.
Figure 9B:
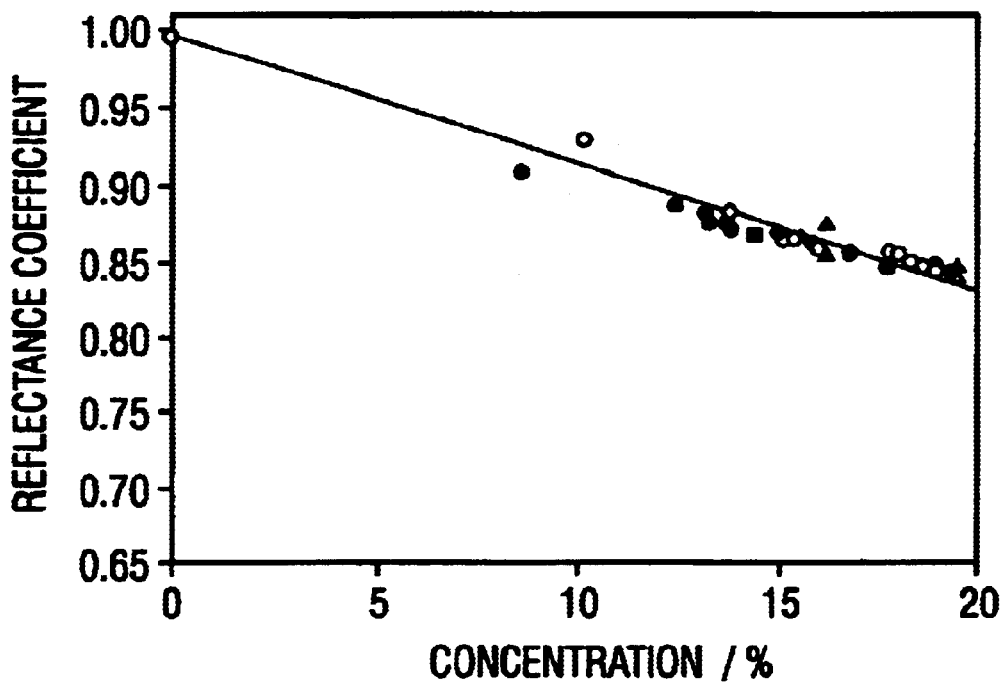

For all samples at all stages of dissolution the ultrasonic reflectance signal was proportional to the amount of dissolved material present (FIG. 9). Ultrasonic reflectance can therefore be used to measure the amount of dissolved powder in a complex mixture containing undissolved crystals. The kinetics of the dissolution processes were typical of powders and depended on the temperature, particle size and composition.

The polymer delay line used in this example can be replaced with the wall of a pipe or piece of process equipment so the dissolution/precipitation measurements could be made without disrupting manufacture in any way. Very often dissolution/precipitation occurs as a slurry flows down a pipe in which case a series of sensors could monitor the process. In many cases the device can be used in a qualitative mode, using the presence of a time-independent signal as an indication that the process is complete.

Example 3

Self Calibration-Twin Delay Line

In the previous examples, it was necessary to perform a calibration with a material of known properties (e.g., water or air) prior to each analysis. In this example, we describe an embodiment of the invention where calibration is not needed.

A twin element delay line is used composed of two materials with differing ultrasonic properties (FIG. 10b). The oscilloscope will therefore detect two echoes; from the junction between the materials used in the delay line (Reflection 1) and from the interface with the material under investigation (Reflection 2). As there are two measured parameters for the two unknowns (ultrasonic properties of the material under investigation and magnitude of the original pulse) the ultrasonic properties of the sample can be measured without resorting to an external calibration.

The material and dimensions for the delay line construction are crucial to the operation of this design. Specifically the materials must be (1) sized so the echoes and reverberations from the pulse do not overlap and (2) have an appropriate acoustic mismatch to produce a measurable echo from their interface and the interface with the sample. These requirements can be quantified as follows:

Avoiding Echo Overlap

In order to avoid the overlap of echoes, the thickness of the two media have to be chosen carefully. Defining the speed of sound and the thickness of medium 1 as $c_1$ and $d_1$, and the speed of sound and the thickness of medium 2 as $c_2$ and $d_2$, we obtain that:

$$t_1 = \frac{2d_1}{c_1} \qquad [5]$$

$$t_2 = \frac{2d_1}{c_1} + \frac{2d_2}{c_2}$$

Here $t_1$ is the time taken by the sound to travel through medium 1, bounce at the interface between the two media and travel back to the transducer and $t_2$ is the time taken by the sound to travel through medium 1 and 2, be reflected by the interface between medium 2 and the sample and travel back to the transducer. The condition that has to be respected in order to avoid overlapping is that:

$$t_1 n \neq t_2 \qquad [6]$$

where n is an integer (the number of reverberations that occur when the sound travels back and forth in medium 1). The pulses have a finite duration so it is useful to perform this calculation for the start and end of the sound envelope.

Adjusting Echo Amplitude

For ease of measurement it is advantageous for the two echoes under consideration to have a similar magnitude. According to the definition of reflectance (transmittance), the amount of sound that it reflected (transmitted) at the interface of two materials depends on the difference in their acoustic impedance as follows:

$$R = \left(\frac{Z_2 - Z_1}{Z_2 + Z_1}\right)^2 \qquad [7]$$

$$T = \frac{4Z_1 Z_2}{(Z_1 + Z_2)^2} \qquad [8]$$

The greater is the difference in acoustic impedance ($Z = \rho c$) between the two materials, the greater the amount of sound reflected at their interface. In the design of the twin delay line is important to use two materials that are acoustically similar, in order to obtain echo 2 with an intensity (amplitude) with the same order of magnitude as echo 1. We have constructed a working twin delay line for measuring the properties of liquids. In this case medium 1, is aluminum ($Z = 17 \times 10^6$ kg.m$^2$s$^{-1}$) and medium 2, is brass ($Z = 37.3 \times 10^6$ kg.m2s$^{-1}$). Using the calculations set out above the suitable echoes from water have respectively amplitudes of 13% and 10% of the original signal magnitude.

Example 4

Solid Fat Content

The solid fat content (SFC) is crucial to the texture of various food products such as chocolate, butter, margarine and shortenings. SFC may change during manufacturing and storage of these products; therefore, it is important to be able to measure this parameter to control the ingredients and manufacturing conditions used for optimum product quality.

Amongst the first procedures used for accurate determination of SFC is dilatometry, which remains a recommended method of the American Oil Chemists Society. This technique measures the solid fat index from the changes in sample density with temperature. The amount of solids in a fat is then estimated empirically from the solid fat index. Dilatometry remains an extremely precise technique but is somewhat laborious and has been replaced in many applications by low resolution NMR. The NMR methods are rapid and easy to use; however, they are poorly sensitive to low concentrations of solid fat.

Solid fat content depends strongly on temperature and temperature history; therefore, one of the biggest obstacles to making good measurements is simulating process/use conditions inside the apparatus or moving sample from the process line to the instrument without causing significant changes. A more direct approach to studying how processing affects SFC, would be to use an on-line sensor. Unfortunately, neither of the approved methods is entirely appropriate for on-line application. In this example we demonstrate how ultrasound can be practically applied to the on-line determination of SFC.

Sample Preparation

Confectionery coating fat (CCF, Van den Bergh Food Ingredients, CLSP870 non-lauric cocoa butter substitute "high trans", Joliet, Ill.) and cocoa butter (CB, Natra, Chula Vista, Calif.) were dispersed in corn oil. Coating fat is typically a non-lauric non-stabilizing fat with a stable polymorphic form that does not require a tempering procedure. Cocoa butter is a polymorphic fat, which requires tempering to guarantee a stable form. According to the official AOCS method, tempering cocoa butter for extended time allows crystallization in a b-form.

The cocoa butter dispersions (26, 28, 30, 32 and 36 wt %) were equilibrated according to the AOCS official method for stabilizing fats (Cd 16b-93, AOCS 1995). After melting at 100° C., the samples were cooled to 0° C. for 90 min and then stored at 26° C. for 40 hours. After this period, they were re-cooled to 0° C. for 90 min and then equilibrated at each chosen measuring temperature (26, 27.5 or 29° C.) for 90 minutes. The dispersions of coating fat (cocoa butter) were tempered without agitation according to a modification of the AOCS official method for non-stabilizing fats (Cd 16b-93, AOCS 1995). Molten coating fat dispersions (5, 7.5, 10, 12.5 and 15 wt %) were equilibrated at 0° C. for six hours followed by six hours at each final measuring temperatures (10, 12 and 15° C.). The SFC of the tempered fat samples was measured in triplicate by pulsed NMR (Minispec mq20, Bruker, The Woodlands, Tex.) using the AOCS direct protocol.

Dark chocolate (32% fat) fat was purchased from Guittard (Burlingame, Calif.). The chocolate was melted and tempered in a Hilliard temper kettle (Hilliard's, West Bridgewater, Mass.) by an experienced operator. The chocolate mass was held at 50° C. for at least 30 minutes to make sure that all the crystals melted. The mass was then cooled to 28° C. (approximate time 10–15 min) and kept at this temperature for the time necessary to guarantee the formation of crystal nuclei in both stable and unstable form. The chocolate mass was then reheated to 31° C. to melt the unstable crystal forms. Temper adequacy was tested using a temper meter (Tricor Systems Inc, Elgin, Ill.).

The speed of sound and reflection coefficient was measured using a modified pulse-echo technique. An electrical spike signal (Panametrics 500 PR, Waltham, Mass.) was passed to a 2.25 MHz broadband ultrasonic transducer (Panametrics V606), which converted the energy to ultrasound. The pulse of sound traveled into a Plexiglas delay line, and was partially reflected at the plastic-sample interface. The reflected part returned through the delay line to the transducer (echo 1) and the transmitted part traveled through the sample (~1 cm), was reflected from the brass plate and returned through the sample and the delay line to the transducer (echo 2). The transducer reconverted the acoustic signal to an electrical signal, which was stored for analysis with a digital oscilloscope (LeCroy 9310c, Chestnut Ridge, N.Y., USA).

The time difference between echo 1 and echo 2 was used to measure the ultrasonic velocity in the sample in conjunction with a water calibration. The proportion of the energy reflected at the interface between the Plexiglas delay line and the sample is given by the reflectance coefficient (Ra) and is related to the acoustic and physical properties of the component materials as follows.

$$R_a = \frac{A_r^2}{A_i^2} = \left(\frac{Z_2 - Z_1}{Z_1 + Z_2}\right)^2 \quad [9]$$

where Z1 and Z2 is the acoustic impedance ($=\rho c$) of the sample and the delay line and $\rho$ is the density. $A_r$ and $A_i$ are the amplitudes of reflected and incident waves respectively. For a given delay line, the peak-to-peak amplitude of echo 1 ($A_r$ in the equation above) depends on the magnitude of the generated pulse (a property of the apparatus) and the acoustic dissimilarity between sample and delay line (a property of the material under investigation). Because the magnitude of the generated pulse could not be directly measured or relied upon as a constant on a day-to-day basis, the measured value was normalized to a similar measurement made against a calibration material (i.e., corn oil) at the measurement temperature. For chocolate tempering measurements, the reflectance from the molten chocolate at 50° C. was used as the calibrant and all subsequent measurements were normalized to this value.

By varying the temperature and composition of a series of CB and CCF dispersions, it was possible to generate a series of dispersions with different SFC (0–9%). The trend of increasing SFC with solids loading and decreased temperature can be seen in Table 2. The endothermic melting peak of CB dispersions tempered at different measuring temperatures. The magnitude of the melting peaks decreases with increased tempering temperature and is proportional to the SFC of similar samples measured by NMR (Table 2). The magnitudes of the melting endotherms of the CCF dispersions (thermograms not shown) were also proportional to the SFC (Table 2). Table 2 shows solid fat content (by NMR) and enthalpy of melting (by DSC) of 15 wt % CCF and 36 wt % CB dispersions tempered to various temperatures.

TABLE 2

| Fat | Temperature | SFC/% | Enthalpy of melting/ $Jg^{-1}$ |
|---|---|---|---|
| CCF | 10° C. | 8.66 ± 0.03 | 69.0 ± 1.5 |
|  | 12° C. | 7.26 ± 0.09 | 52.8 ± 2.0 |
|  | 15° C. | 4.96 ± 0.07 | 39.7 ± 1.2 |

TABLE 2-continued

| Fat | Temperature | SFC/% | Enthalpy of melting/ Jg$^{-1}$ |
|---|---|---|---|
| CB | 26° C. | 4.09 ± 0.06 | 22.7 ± 3.1 |
|  | 27.5° C. | 2.10 ± 0.20 | 10.2 ± 1.3 |
|  | 29° C. | 0.58 ± 0.21 | 3.1 ± 0.4 |

Figure 11:
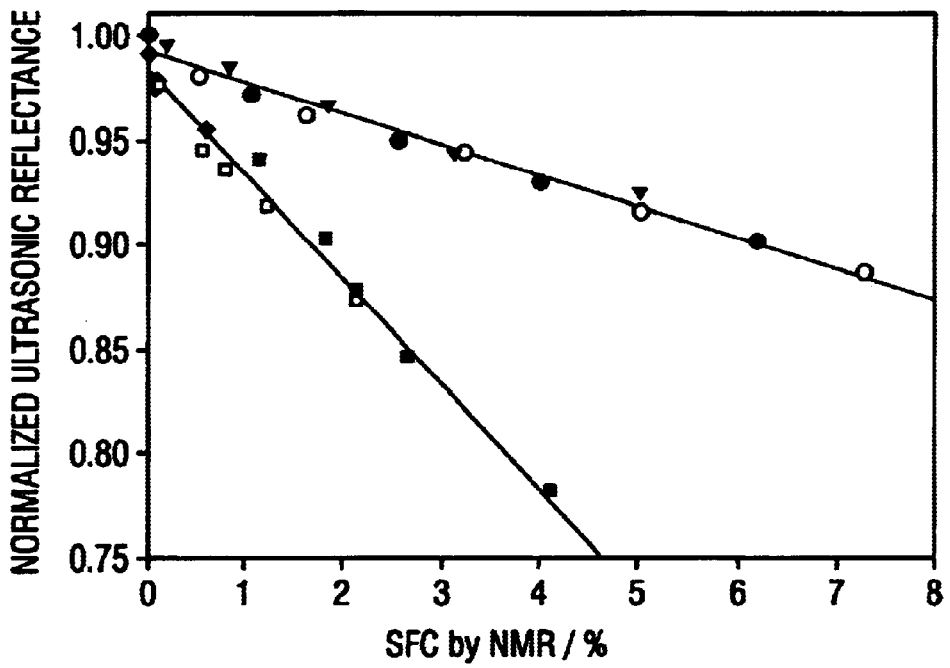
FIG. 11 shows a plot of the normalized ultrasonic reflectance of the confectionary coating fat (CCF) and cocoa butter (CB) dispersions versus solid fat content (SFC) % determined by NMR as in Example 4.

Increasing the SFC led to a linear decrease in normalized ultrasonic reflectance of the CCF and CB dispersions (FIG. 11). The decreased reflectance is because the increase in SFC makes the sample more acoustically similar to the Plexiglas delay line and therefore the interface less reflective. Typical coefficients of variance for determination of SFC by reflectance measurements 0.6 and 0.9% for coating fat and cocoa butter respectively.

For a given fat system both ultrasonic velocity (if measurable) and ultrasonic reflectance can be used to measure the SFC. The precision of both methods is similar to NMR, and both methods are superior to NMR in distinguishing between samples with low solids contents. Reflectance is perhaps a more generally useful method as it can be conducted on highly attenuating fats such as cocoa butter. However, while the ultrasonic properties measured vary strongly with SFC, there are differences between the acoustic properties of CB and CCF at the same levels of solids.

Figure 12:
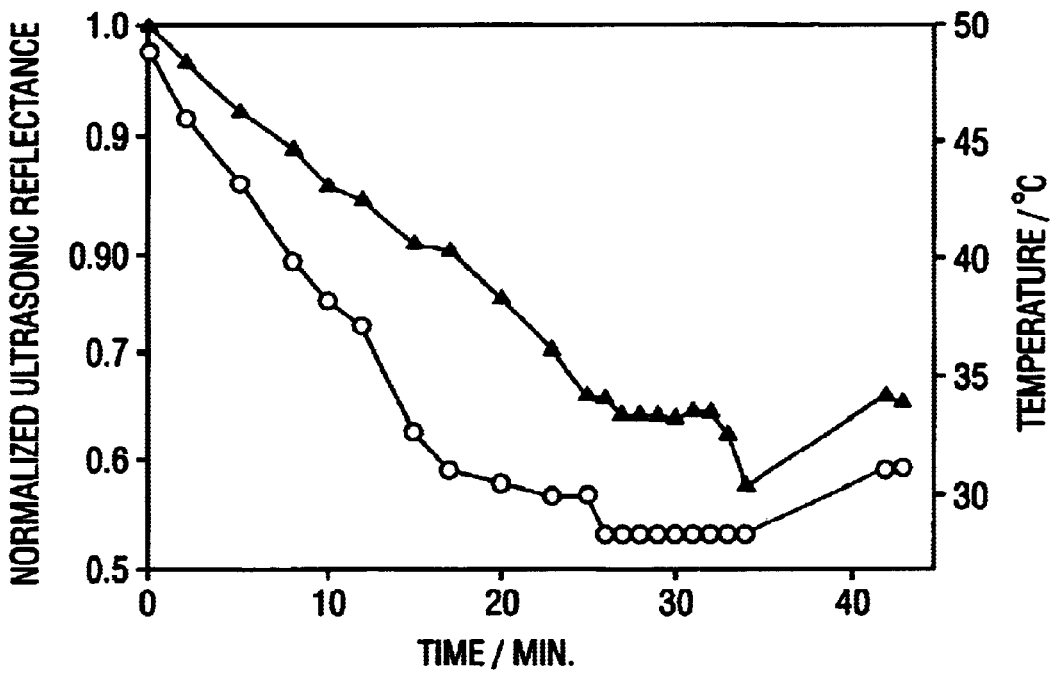
FIG. 12 shows a plot of the normalized ultrasonic reflectance of the confectionary coating fat (CCF) and cocoa butter (CB) dispersions in Example 4 over time.

The strong sensitivity of ultrasonic reflectance to SFC provides a basis for an online temper meter. As a demonstration, a batch of chocolate was tempered in a Hilliard temper kettle. The time temperature plot is shown in FIG. 12. The ultrasonic reflectance was measured continuously as the chocolate was tempered and the results are also shown alongside the time-temperature data. The ultrasonic reflectance decreased with temperature during the initial cooling phase of the process and remains unchanged during the initial part of the isothermal phase until at approximately 33 min there was a sudden decrease in reflectance. We have seen in FIG. 11 that a decrease in reflectance is associated with an increase in SFC and we hypothesize that we are seeing the onset of crystallization in the chocolate mass at 33 min. Samples of chocolate withdrawn before this time were slightly under tempered by the off-line Tricor temper meter while the degree of temper increased rapidly after this time. The degree of tempering was also tested by molding the chocolate mass. Samples of chocolate molded before this time were dull and did not have a good texture; while samples molded immediately after this time formed glossy chocolate with a good "snap".

While the invention has been particularly shown and described with reference to preferred embodiments thereof, it will be understood by those skilled in the art that various alterations in form and detail may be made therein without departing from the spirit and scope of the invention. In particular, the delay line(s) of the invention can be made from different materials and shapes within the constraints mentioned above. Additionally, it is within the abilities of one of ordinary skill in the art to implement the present invention in a number of ways as to how the invention is connected to or used with food processing equipment. Such modification are considered to be within the scope of the present invention.

What is claimed is:

1. An ultrasonic device for measuring one or more physical properties of a fluid body, wherein said device is designed to be used with a twin delay line and comprises:
   a) means for transmitting ultrasonic longitudinal waves;
   b) a first delay coupled with the transmitting means and capable of being coupled to the fluid container wall as the second delay line;
   c) means for measuring reflected ultrasonic longitudinal echoes;
   d) means for self calibrating the device using echoes from the interface of the first and second delay lines and the second delay line-fluid interface; and
   e) means for calculating one or more physical properties of the fluid body from the fluid interface reflected echo measurements.

2. The device of claim 1 which is solid concentration sensor.

3. The device of claim 1 which is a dissolution sensor.

4. The device of claim 1 which is a solid fat content sensor.

5. The device of claim 1 wherein the calculation means comprises software or circuitry based on an empirically predetermined linear or non-linear function.

6. The device of claim 1 wherein one of the delay lines is a polymer.

7. A method of measuring one or more physical properties of a fluid food in a food processing system, said method comprising:
   a) coupling the device of claim 1 to the container holding said fluid food;
   b) generating ultrasonic longitudinal waves;
   c) allowing the longitudinal waves to transmit through the first delay line and the container acting as a second delay line, whereby longitudinal waves are reflected from the interface between the first and second delay lines and from the interface between said container/ second delay line and said fluid food;
   d) detecting the reflected ultrasonic longitudinal echoes from both interfaces;
   e) self calibrating the device using the detected reflected echoes from both interfaces; and
   f) calculating one or more physical properties of the fluid body using the detected echoes reflected from the container-fluid interface.

8. A method of measuring one or more physical properties of a fluid food in a food processing system wherein said physical property is directly or indirectly related to the bulk modulus of the fluid, said method comprising:
   a) generating ultrasonic longitudinal waves;
   b) coupling said waves to the container holding said fluid food;
   c) detecting reflected ultrasonic longitudinal waves from the interface between said container and said fluid food;
   d) using characteristics of said waves reflected from said interface to determine one or more physical properties of the fluid food; and
   e) self-calibrating via a twin delay line, wherein the twin delay line comprises two different materials providing different echoes which are used for self-calibration.

9. A method of measuring one or more physical properties of a fluid food in a food processing system wherein said physical property is directly or indirectly related to the bulk modulus of the fluid, said method comprising:
   a) generating ultrasonic longitudinal waves;
   b) coupling said waves to the container holding said fluid food;
   c) detecting reflected ultrasonic longitudinal waves from the interface between said container and said fluid food;

d) using characteristics of said waves reflected from said interface to determine one or more physical properties of the fluid food e) comparing the measured reflectance amplitude with a previously empirically determined linear or non-linear function for the physical property being investigated; and f) using a linear calibration function $X = X_{water} + k\phi$, where X is the normalized reflection amplitude of the sample, $X_{water}$ is the normalized reflection amplitude of calibrant fluid, k is a constant determined by linear regression, and $\phi$ is the solids content of the sample.

10. A method of measuring one or more physical properties of a fluid food in a food processing system wherein said physical property is directly or indirectly related to the bulk modulus of the fluid, said method comprising:

a) generating ultrasonic longitudinal waves;

b) coupling said waves to the container holding said fluid food;

c) detecting reflected ultrasonic longitudinal waves from the interface between said container and said fluid food;

d) using characteristics of said waves reflected from said interface to determine one or more physical properties of the fluid food;

e) self-calibrating via a twin delay line, wherein the twin delay line comprises two different materials providing different echoes which are used for self-calibration; and wherein the container wall is one of the delay lines.

* * * * *

UNITED STATES PATENT AND TRADEMARK OFFICE
CERTIFICATE OF CORRECTION

PATENT NO.        : 6,912,891 B2
APPLICATION NO.   : 10/177694
DATED             : July 5, 2005
INVENTOR(S)       : John N. Coupland et al.

It is certified that error appears in the above-identified patent and that said Letters Patent is hereby corrected as shown below:

Col. 1, line 9 should read as follows:
This invention was made with government support under Hatch Act Project Nos. PEN03591 and PEN03697, awarded by the USDA. The Government has certain rights in the invention.

Signed and Sealed this

Twenty-sixth Day of October, 2010

David J. Kappos
*Director of the United States Patent and Trademark Office*